United States Patent [19]
Klingler et al.

[11] Patent Number: 5,330,454
[45] Date of Patent: Jul. 19, 1994

[54] OSTOMY APPLIANCE WITH FLOATING BELT-ATTACHMENT RING

[75] Inventors: Wayne P. Klingler; Walter F. Leise, Jr., both of Lindenhurst, Ill.

[73] Assignee: Hollister Incorporated, Libertyville, Ill.

[21] Appl. No.: 78,820

[22] Filed: Jun. 21, 1993

[51] Int. Cl.⁵ .................................................. A61F 5/44
[52] U.S. Cl. ...................................... 604/338; 604/342
[58] Field of Search .................................. 604/332–345

[56] References Cited

U.S. PATENT DOCUMENTS

| | | | |
|---|---|---|---|
| 3,523,534 | 8/1970 | Nolan | 128/283 |
| 3,822,704 | 7/1974 | Nolan | 128/283 |
| 4,213,458 | 7/1980 | Nolan et al. | 128/283 |
| 4,419,100 | 12/1983 | Alexander | 604/339 |
| 4,477,325 | 10/1984 | Osborn | 204/159.12 |
| 4,496,357 | 1/1985 | Osborn | 604/336 |
| 4,710,182 | 12/1987 | Bryson | 604/339 |
| 4,834,731 | 5/1989 | Nowak et al. | 604/339 |
| 4,973,323 | 11/1983 | Kaczmarek et al. | 604/339 |

*Primary Examiner*—Randall L. Green
*Assistant Examiner*—Rob Clarke
*Attorney, Agent, or Firm*—Tilton Fallon Lungmus

[57] ABSTRACT

An ostomy appliance in which a collection pouch is provided with an adhesive faceplate, that may be equipped with a convex pressure ring, and in which a relatively stiff belt-attachment ring is interposed between the pouch and faceplate. Despite the stiffness of the belt-attachment ring and that of the convex pressure ring normally in close proximity it, the tab connectors of the attachment ring are readily accessible because the belt-attachment ring is supported in a limited "floating" condition by a thin, highly-flexible, annular web. The web is secured to both the pouch and faceplate along an inner first sealing zone and joins the belt-attachment ring along a second concentric sealing zone spaced a substantial distance outwardly from the first zone.

10 Claims, 2 Drawing Sheets

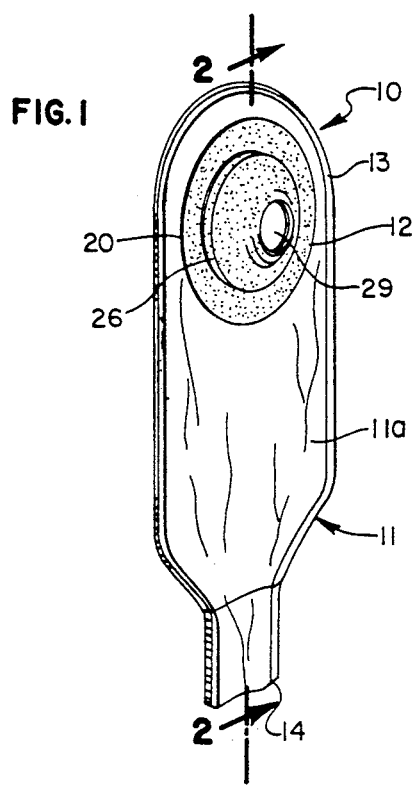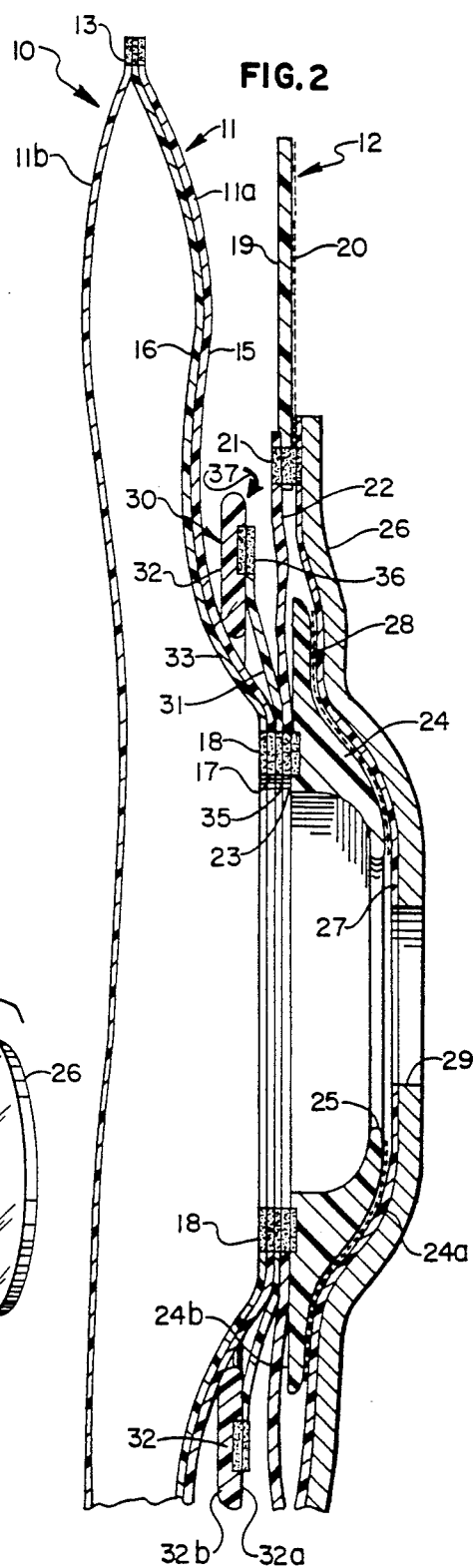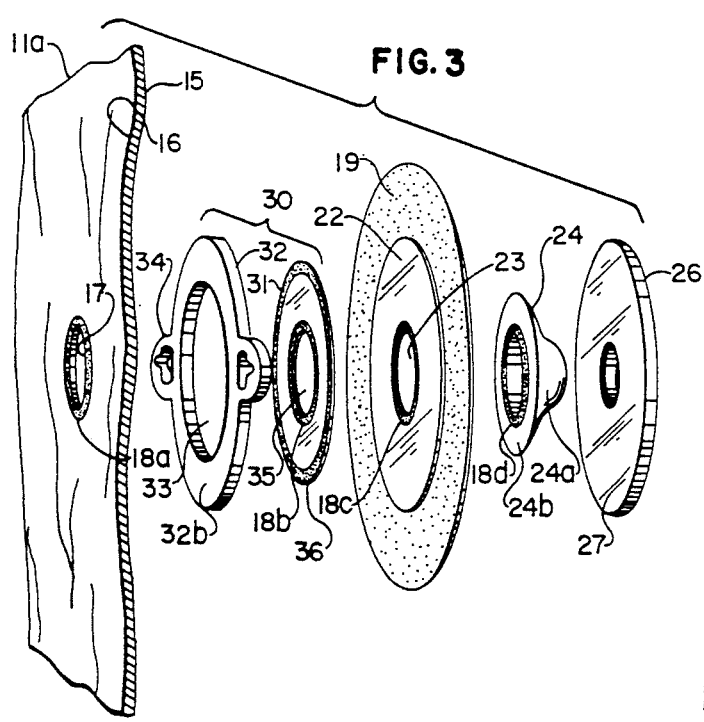

FIG. 4
FIG. 5
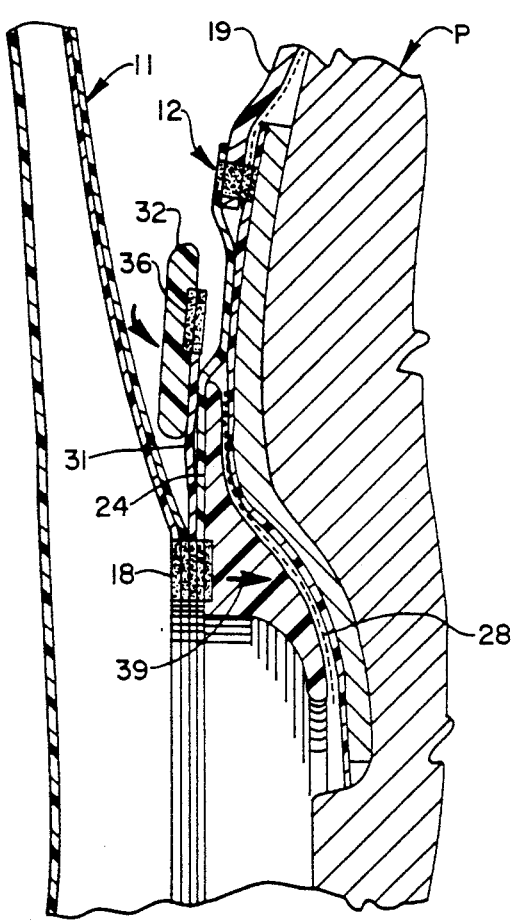
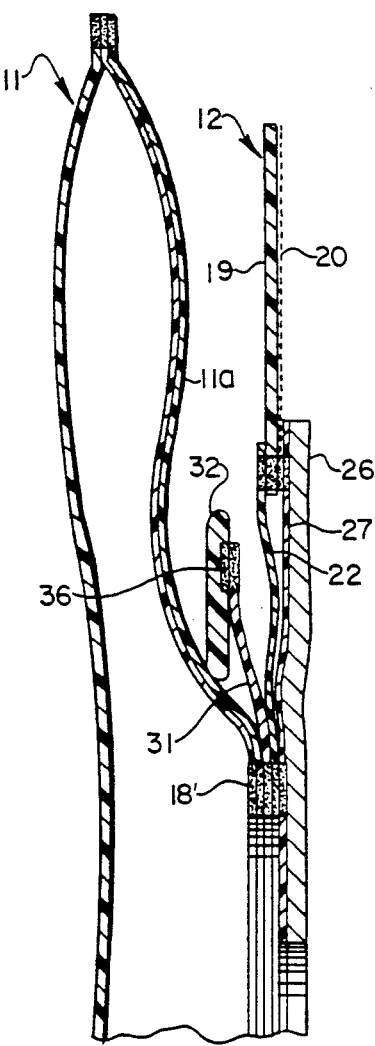

OSTOMY APPLIANCE WITH FLOATING BELT-ATTACHMENT RING

BACKGROUND AND SUMMARY

One-piece ostomy appliances are often provided with belt-attachment rings so that a wearer may connect a support belt to the appliance to provide additional security in holding it in place. The term "one-piece" as commonly used in this field means a unitary appliance in which the pouch and adhesive faceplate are permanently joined together, in contrast to a two-piece appliance in which a pouch and faceplate are detachably connected by a pair of mechanical (or adhesive) coupling rings. One-piece appliances equipped with such belt-attachment rings are disclosed, for example, in co-owned U.S. Pat. Nos. 3,523,534, 3,822,704 and 4,213,458. Belt-attachment rings, where they are provided, are usually heat sealed or otherwise secured to the pouches, although co-owned U.S. Pat. No. 4,710,182 discloses a construction in which a separate belt-attachment ring may be added by the patient by first collapsing the pouch and inserting it through the opening of the ring until the ring is in the position depicted in FIG. 4 of that reference.

It is also known to provide ostomy appliances with relatively rigid convex pressure rings for the purpose of increasing stomal protrusion when the appliance is worn, thereby aiding in the discharge of effluent directly into the pouch and also prolonging the effectiveness of the adhesive seal between the faceplate and peristomal skin surfaces. Reference may be had to U.S. Pat. Nos. 4,834,731 and 4,973,323 for examples of appliances having such pressure rings.

Where an appliance is equipped with both a convex pressure ring and a belt-attachment ring, the close proximity of the two rings and their stiffness may make it difficult for a wearer to connect or disconnect a belt from the connecting loops or tabs of the belt-attachment ring. Even where a convex pressure ring is absent, it may be difficult for a wearer to fit his/her fingers between the connecting tabs of the belt-attachment ring and the adhesive faceplate because of the stiffness of the ring and the close proximity of the annular area of connection between the ring and the faceplate on which it is mounted. Also, it has been found that the customary stiffness of a belt-attachment ring may have the undesirable effect of interfering with the flexibility of those portions of an adhesive faceplate that should be free to conform to the anatomical contour of peristomal body surfaces and to changes in such contour as a patient moves about.

One aspect of this invention therefore lies in providing an ostomy appliance with a belt-attachment ring that does not impair the flexibility and conformability of an adjoining faceplate and that also allows a user to shift the belt-attachment ring away from the faceplate to facilitate access to the connecting tabs of the ring when a belt is to be attached to or detached from the appliance. All of this is achieved while at the same time providing a construction in which there exists a positive connection between the belt-attachment ring and the remainder of the appliance, thereby assuring that the belt-attachment ring will remain properly oriented with respect to other components of the appliance when that appliance is worn with a supporting belt.

Briefly, the appliance of this invention including a relatively stiff belt-attachment ring which extends about the periphery of a thin, highly-flexible, annular web. The annular web has its inner margin joined to the pouch and faceplate along a first attachment zone concentric with the ring and spaced a substantial distance radially inwardly from that ring. Consequently, the belt-attachment ring is supported for limited floating action, with freedom to move limited distances in axial directions, independent of the pouch and faceplate. Because of such floating action, the belt-attachment ring does not impair flexibility of the faceplate and its ability to conform to peristomal surfaces, and the ring may be easily urged axially away from the faceplate to a limited extent to facilitate attachment and detachment of a belt while the appliance is worn.

Other features, advantages, and objects of the invention will appear from the specification and drawings.

DRAWINGS

FIG. 1 is a perspective view of an ostomy appliance embodying the present invention.

FIG. 2 is a somewhat schematic enlarged vertical sectional view taken along line 2—2 of FIG. 1 and, for illustrative purposes, depicting the belt-attachment ring urged away from the faceplate (and towards the pouch) to a limited extent.

FIG. 3 is an exploded perspective view showing components illustrated in FIG. 2.

FIG. 4 is an enlarged fragmentary sectional view similar to FIG. 2 but showing the relationship of parts as they might exist when the appliance is worn with a belt in place.

FIG. 5 is a vertical sectional view of an appliance similar to that of FIGS. 1-4 except for the absence of a convex pressure ring.

DETAILED DESCRIPTION OF PREFERRED EMBODIMENTS

Referring to FIGS. 1-4, the numeral 10 generally designates an ostomy appliance including a pouch 11 and a faceplate 12. The pouch is generally flat and includes front and rear walls 11a and 11b sealed together along their peripheral edges by heat seal 13. In the illustration given, the pouch is a drainable one having an opening 14 adapted to be folded and sealed by a suitable closure such as a clip of the type disclosed in co-owned U.S. Pat. No. 3,523,534; however, it is to be understood that this invention may be used equally well with non-drainable appliances.

The pouch may be formed of any suitable thermoplastic film such as low-density polyethylene which, if desired, may be coextruded with a barrier core material such as polyvinylidene chloride. Any suitable thermoplastic film materials that are impermeable to liquids and gases may be used. In the embodiment illustrated, front wall 11a is composed of two layers 15, 16, the outer layer 15 consisting of a thermoplastic non-woven fabric for increasing softness, quiteness and wearer comfort, although it is to be understood that such a fabric layer is optional. Layer 16 may be formed of the same thermoplastic film material as rear wall 11b.

As depicted most clearly in FIGS. 2 and 3, front wall 11a has a stoma-receiving opening 17 formed therein. The two layers 15, 16 of the front wall are joined together about that opening in an annular heat seal zone 18.

Faceplate 12 includes a thin, flexible outer patch or ring 19 coated on its front or bodyside surface with a pressure-sensitive adhesive represented by dotted lines 20 in FIG. 2. The patch 19 may be gas permeable, or at least moisture vapor permeable, to allow the escape of moisture from the skin. A breathable microporous material of the type disclosed in U.S. Pat. No. 4,213,458 may be used, although any of a variety of other known tape-like materials are believed suitable. The inner margin of the annular patch is secured by annular heat seal 21 to the outer margin of a thin, flexible, thermoplastic inner ring 22. As shown clearly in FIG. 2, the inner ring defines an opening 23 in register with stoma opening 17 of the pouch and is joined to the pouch by the same heat seal 18 that secures layers 15 and 16 together.

The advantages of providing the faceplate with both an outer patch ring 19 and an inner connecting ring 22 are discussed at length in U.S. Pat. No. 4,213,458. The inner ring 22 is formed of ethyl vinyl acetate or any other film material that is relatively strong and capable of being securely heat sealed to the pouch as well as to the outer patch ring 19. The inner ring therefore distributes forces to maintain a secure connection between the faceplate and the pouch when the appliance is in use. Since the inner ring 22 is non-porous, there is no danger of liquids wicking outwardly through ring 22 and into the outer patch ring 19 when the appliance is in use.

Faceplate 12 also includes a relatively rigid pressure ring 24 having a central opening 25 and a convex front or bodyside surface 24a. The term "relatively rigid" is here used to mean that the ring retains its distinctive shape under normal conditions of use. While various materials may be used for ring 24, rigid or semi-rigid plastics such as polypropylene, polyethylene, or polystyrene are considered particularly suitable. It will be observed that ring 24 has a planar rear or pouchside surface 24b and is heat sealed to other components of the appliance by the same heat seal 18 that joins film ring 22 to pouch 11.

A layer 26 of skin barrier material, backed by a thermoplastic film 27, is secured to the contoured face of pressure ring 24 by a layer of adhesive 28. The adhesive may be the same as the pressure-sensitive adhesive coating 20 of patch 19 and may take the form of a medical-grade acrylic adhesive of a type well known in this field. Alternatively, a conventional hot-melt adhesive may be used. Layer 26 is annular in shape, having a central opening 29 aligned with openings 25, 23, and 17 of the pressure ring, inner connecting ring 22 and pouch, respectively. The backing film 27 of the barrier layer or ring 26 has its outer margin secured to patch 19 by the same annular heat seal 21 that joins the patch to inner ring 22.

Skin barrier ring or layer 26 is formed of a soft, pliable, water-absorbing material having both dry and wet tack. A variety of such compositions are known in the art and may be used here. Karaya-glycerin formulations, mixtures of polyacrylamide resin and other polyols, and mixtures of elastomers and hydrocolloids are believed suitable. Reference may be had to U.S. Pat. Nos. 4,477,325 and 4,496,357 for a discussion of skin barrier compositions having advantages which may also be utilized here. Belt-attachment means 30 are interposed between pouch 0 and faceplate 12. Such means takes the form of a thin, highly-flexible annular web 31 and a relatively stiff belt-attachment ring 32. The belt-attachment ring is flat and has an opening 33 substantially larger than the openings of pouch wall 11a, inner ring 22, and convex pressure ring 24. Apertured belt-attachment tabs or loops 34 extend laterally from the perimeter of ring 32 for detachable connection to the clips or connectors of a support belt (not shown) in a manner well known in the art. As shown in FIG. 2, the attachment ring has flat parallel faces 32a and 32b with the radial dimensions of each of those faces being substantially greater than the thickness of the ring.

Annular web 31 has an opening 35 in register with openings 23 and 17 of inner ring 22 and pouch wall 11a, respectively. The same heat seal 18 that welds the pouch wall to the inner ring 22 and to convex pressure ring 24 also secures the inner margin of web 31 in place. The web therefore has an inner edge portion secured by first heat seal 18 to the pouch and faceplate and an outer edge portion secured by second heat seal 36 to one face (face 32a) of the stiff belt-attachment ring 32. The second heat seal zone is concentric with the first heat seal zone and is spaced substantially outwardly from the first zone. The second heat seal 36 is also preferably spaced radially outwardly beyond the edge that defines opening 33 of the belt-attachment ring. As a result, there is a substantial radial extent of web 31 between heat seals 18 and 36 and, because of the flexibility of the thin and generally planar web 31, the belt-attachment ring may easily be shifted axially one way or the other to permit gripping of the ring by a user and to facilitate attachment of a belt to apertured tabs 34. Thus, in FIG. 2 the belt-attachment ring 32 is shown as being displaced towards the left, in response to forces exerted in the direction of arrows 37. Conversely, when a waist-encircling support belt is attached and tightened, the belt-attachment ring will be drawn to the right as depicted in FIG. 4.

Referring to FIG. 3, the parts that are joined together by the first heat seal 18 are shaded to indicate the portions that are welded together. Thus, the first heat seal 18 is composed of portions 18a, 18b, 18c, and 18d (of wall 16, web 31, film ring 22, and convex pressure ring 24, respectively) that secures the parts together in a single heat sealing operation. At the time the heat sealing operation is performed, belt-attachment means 30 already exists as a sub-assembly; that is, belt-attachment ring 32 is already joined by the second heat seal 36 to the outer periphery of web 31.

Web 31 may be formed of any thin, highly-flexible thermoplastic film of a thickness generally falling within the range of 1 to 6 mils. An EVA film of 2 mil thickness has been found particularly effective but other thermoplastic film materials having similar properties may be used.

It will be observed that the diameter of ring opening 33 is smaller than the outside diameter of convex pressure ring 24. Therefore, when the appliance is adhesively applied to a patient P and the belt (not shown) conventionally attached to apertured tabs 34 is tightened, the belt-attachment ring 32 is drawn into contact with faceplate 12 and transmits forces to the outer portion of pressure ring 24 to urge the pressure ring (and the faceplate as a whole) in the direction of arrow 39 in FIG. 4.

While the combination of a stiff belt-attachment ring 32 supported for limited floating action by a thin, flexible web 31 is particularly effective in combination with a faceplate 12 having a convex pressure ring 24 for the reasons already indicated, pressure ring 24 may be omitted if desired. A modified construction depicted in FIG. 5 is identical to the embodiment already described except that the convex pressure ring 24 and its adhesive coating 28 are absent. The first annular heat seal 18' joins the front wall 11a of pouch 11, web 31, inner ring 22, and thermoplastic backing film 27 together in a composite weld that holds the belt-attachment means in place, but with freedom for limited axial movement of ring 32, and also secures the multi-element faceplate 12 to collection pouch 11.

It will be understood that in the product as marketed, the bodyside surface of barrier layer 26 and the adhesive layer 20 of patch 19 would be covered by release sheets formed of a suitable material such as siliconized paper. Such release sheets are omitted in the drawings for clarity of illustration.

While in the foregoing, embodiments of the invention have been disclosed in considerable detail for purposes of illustration, it will be understood by those skilled in the art that many of these details may be varied without departing from the spirit and scope of the invention.

We claim:

1. An ostomy appliance comprising a collection pouch formed of thermoplastic film having a wall provided with a stoma opening; a flexible faceplate having pouchside and bodyside surfaces and being provided with pressure-sensitive adhesive means along said bodyside surface for adhesive attachment of said appliance to a wearer; said faceplate having an opening aligned with said pouch opening and being secured to said pouch wall about said pouch opening; and belt-attachment means interposed between said faceplate and pouch and comprising (a) a thin, highly-flexible annular web having an opening defined by an inner edge portion and (b) a relatively stiff belt-attachment ring joined to an outer edge portion of said web; said attachment ring being provided with means for detachably connecting said ring to a body-encircling support belt; whereby, said thin, flexible web supports said belt-attachment ring for limited independent movement towards and away from said fireplate and pouch to facilitate connection and disconnection of said ring and belt by a user when said appliance is worn; said web being thermoplastic and having its inner edge portion interposed between and heat sealed to both said pouch wall and said faceplate along an annular first heat seal zone; said faceplate including inner and outer ring elements; said inner ring element being formed of flexible non-porous thermoplastic material and said outer ring element being formed of moisture vapor permeable material.

2. An ostomy appliance comprising a collection pouch formed of thermoplastic film having a wall provided with a stoma opening; a flexible faceplate having pouchside and bodyside surfaces and being provided with pressure-sensitive adhesive means along said bodyside surface for adhesive attachment of said appliance to a wearer; said faceplate having an opening aligned with said pouch opening and being secured to said pouch wall about said pouch opening; and belt-attachment means interposed between said faceplate and pouch and comprising (a) a thin, highly-flexible annular web having an opening defined by an inner edge portion and (b) a relatively stiff belt-attachment attachment ring joined to an outer edge portion of said web; said attachment ring being provided with means for detachably connecting said ring to a body-encircling support belt; whereby, said thin, flexible web supports said belt-attachment ring for limited independent movement towards and away from said faceplate and pouch to facilitate connection and disconnection of said ring and belt by a user when said appliance is worn; said web being thermoplastic and having its inner edge portion interposed between and heat sealed to both said pouch wall and said faceplate along an annular first heat seal zone; said faceplate including a skin barrier ring having a thermoplastic film backing; said thermoplastic film backing being heat sealed to said web and said pouch along said first heat seal zone.

3. An ostomy appliance comprising a collection pouch formed of thermoplastic film having a wall provided with a stoma opening; a flexible faceplate having pouchside and bodyside surfaces and being provided with pressure-sensitive adhesive means along said bodyside surface for adhesive attachment of said appliance to a wearer; said faceplate having an opening aligned with said pouch opening and being secured to said pouch wall about said pouch opening; and belt-attachment means interposed between said faceplate and pouch and comprising (a) a thin, highly-flexible annular web having an opening defined by an inner edge portion and (b) a relatively stiff belt-attachment ring secured to an outer edge portion of said web; said attachment ring being provided with means for detachably connecting said ring to a body-encircling support belt; whereby, said thin, flexible web supports said belt-attachment ring for limited independent movement towards and away from said faceplate and pouch to facilitate connection and disconnection of said ring and belt by a user when said appliance is worn while preventing rotation of said belt-attachment ring with respect to said pouch and faceplate.

4. The appliance of claim 3 in which said web is thermoplastic and has its inner edge portion interposed between and heat sealed to both said pouch wall and said faceplate along an annular first heat seal zone.

5. The appliance of claim 4 in which said belt-attachment ring has generally planar bodyside and pouchside faces with one of said faces being heat sealed to said outer edge portion of said web in a second heat seal zone spaced substantially outwardly from said first heat seal zone.

6. The appliance of claim 3 in which said faceplate includes a relatively rigid thermoplastic pressure ring having a convex surface facing away from said pouch and having a generally planar surface facing toward said web and pouch wall; said pressure ring having an opening coaxial with the pouch's stoma opening; said pressure ring also being sealed to said web and pouch along said first heat seal zone.

7. The appliance of claim 6 in which said pressure ring has an outside diameter greater than the inside diameter of said belt-attachment ring.

8. The appliance of claim 5 in which said second heat seal zone is located along one of said planar faces of said belt-attachment ring.

9. The appliance of claim 8 in which said second heat seal zone is spaced from the inner periphery of said belt-attachment ring.

10. The appliance of claim 9 in which said second heat seal zone is located along said bodyside face of said belt-attachment ring adjacent the outer periphery thereof.

* * * * *

UNITED STATES PATENT AND TRADEMARK OFFICE
CERTIFICATE OF CORRECTION

PATENT NO. : 5,330,454
DATED : July 19, 1994
INVENTOR(S) : Wayne P. Klingler and Walter F. Leise, Jr.

It is certified that error appears in the above-identified patent and that said Letters Patent is hereby corrected as shown below:

Column 5, line 37, cancel "fireplate" and
    substitute "faceplate"

Signed and Sealed this

Thirteenth Day of September, 1994

Attest:

BRUCE LEHMAN

Attesting Officer

Commissioner of Patents and Trademarks